(12) United States Patent
Rioux et al.

(10) Patent No.: US 7,691,058 B2
(45) Date of Patent: Apr. 6, 2010

(54) SURGICAL RETRACTOR DEVICE AND METHOD OF USE

(75) Inventors: Robert F. Rioux, Ashland, MA (US); Dino D. Buro, Carle Place, NY (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 454 days.

(21) Appl. No.: 11/424,483

(22) Filed: Jun. 15, 2006

(65) Prior Publication Data

US 2007/0293730 A1 Dec. 20, 2007

(51) Int. Cl.
*A61B 1/32* (2006.01)
(52) U.S. Cl. ........................... 600/233; 600/231
(58) Field of Classification Search ............... 600/210, 600/215–217, 231–233
See application file for complete search history.

(56) References Cited

U.S. PATENT DOCUMENTS

| | | | | |
|---|---|---|---|---|
| 2,053,868 | A * | 9/1936 | Grosso | 600/233 |
| 4,274,398 | A | 6/1981 | Scott, Jr. | |
| 4,434,791 | A * | 3/1984 | Darnell | 600/233 |
| RE32,021 | E * | 11/1985 | Scott, Jr. | 600/217 |
| 4,622,955 | A * | 11/1986 | Fakhrai | 600/217 |
| 5,580,344 | A | 12/1996 | Hasson | |
| 5,984,866 | A * | 11/1999 | Rullo et al. | 600/231 |
| 6,048,309 | A | 4/2000 | Flom et al. | |
| 6,241,659 | B1 * | 6/2001 | Bookwalter et al. | 600/231 |
| 6,488,621 | B1 | 12/2002 | Rullo et al. | |
| 2003/0195392 | A1 * | 10/2003 | Hamel et al. | 600/213 |
| 2004/0015185 | A1 * | 1/2004 | Ewers et al. | 606/213 |
| 2004/0186356 | A1 * | 9/2004 | O'Malley et al. | 600/231 |

FOREIGN PATENT DOCUMENTS

| FR | 2662332 A1 * | 11/1991 |
|---|---|---|
| WO | WO2005070303 | 8/2005 |

OTHER PUBLICATIONS

PCT International Search report for PCT/US2007/070793, Applicant: Boston Scientific Scimed, Inc., Form PCT/ISA/210 and 220, dated Apr. 22, 2007 (9 pages).*
PCT Written Opinion of the International Search Authority for PCT/US2007/070793, Applicant: Boston Scientific Scimed, Inc., Form PCT/ISA/237, dated Apr. 22, 2007 (8 pages).*
PCT Communication Relating to the Results of the Partial International Search, Form PCT/ISA/206, for PCT/US2007/070793; Applicant: Boston Scientific Scimed, Inc., dated Jan. 3, 2008 (4 pages).
Aloia, Thomas A., et al., "Two-Surgeon Technique for Hepatic Parenchymal Transection of the Noncirrhotic Liver Using Saline-Linked Cautery and Ultrasonic Dissection", Annals of Surgery, vol. 242, No. 2, Aug. 2005, pp. 172-177.
Unofficial English translation of FR 2662332 ("Couraud") obtained from the European Patent Office website, Jul. 8, 2009, 2 pages.

* cited by examiner

*Primary Examiner*—Eduardo C Robert
*Assistant Examiner*—Julianna N Harvey
(74) *Attorney, Agent, or Firm*—Finnegan, Henderson, Farabow, Garrett and Dunner, LLP (57) ABSTRACT

A surgical retractor device includes a frame and at least one retracting member configured for being secured to the collapsible frame. The retracting member is formed from a spring-biased rotatable member, a tension line secured at a proximal end to the spring-biased rotatable member, and a tissue securing member disposed at a distal end of the tension line. In certain embodiments, the surgical retractor may be collapsible and delivered laparoscopically to the resection site.

14 Claims, 5 Drawing Sheets

SURGICAL RETRACTOR DEVICE AND METHOD OF USE

FIELD OF THE INVENTION

The field of the invention generally relates to surgical retractor devices. More particularly, the field of the invention pertains to surgical retractor devices capable of imparting a biasing force to a portion of tissue. In certain embodiments, the device may be administered laparoscopically.

BACKGROUND OF THE INVENTION

During many surgical procedures, a region of tissue such as an organ is cut or resected by the operating physician. In order to more fully expose a cutting or resection plane, it is known to retract or pull apart the cut tissue. For instance, one or more stay sutures may be secured to the tissue and the sutures may be pulled taught to open or expose the deepening resection plane. As one illustrative example, one known method of performing hepatic parenchymal transaction utilizes polypropylene stay sutures to expose the deepening transaction plane.

The details of this operative technique are disclosed in Aloia et al., *Two-Surgeon Technique for Hepatic Parenchymal Transection of the Noncirrhotic Liver Using Saline-Linked Cautery and Ultrasonic Detection*, Annals of Surgery, Vol. 242, No. 2, August 2005. As described in this publication, two surgeons are required to transect the liver. A first surgeon located on one side of the patient uses an ultrasonic dissection device to dissect the tissue. A second surgeon located on the other side of the patient uses a saline-linked cautery device to coagulate and divide dissected vessels. In addition, to expose the deepening transaction plane, the surgeons manually apply traction on the stay sutures to separate the cut tissue.

While the two-surgeon operative technique provides advantages over prior techniques, the technique requires two surgeons to perform the operation. It would be preferable if a single surgeon could perform the transaction operation. Unfortunately, using the technique disclosed in Aloia et al., a single surgeon cannot dissect and/or coagulate the transected tissue while at the same time applying the necessary traction to the stay sutures to expose the deepening transaction plane.

Surgical retractor devices are also known that eliminate the need for a surgeon (or other person) to manually apply tension to a portion of cut tissue. For example, U.S. Pat. No. 4,274,398 issued to Scott discloses a surgical retractor which includes a frame conformed to fit the surface contour of the portion of the body to be operated on. The frame has a plurality of notches spaced about its periphery. The device further includes a number of elastic stays with hooks that are used to retract the tissue. The elastic portion of the stays is adapted to be inserted into one of the notches and is held in place by friction to retract the tissue.

The retraction device disclosed in Scott, however, is unsuitable for laparoscopic applications. Instead, the device disclosed in Scott includes an annular frame that is conformed to fit the surface contour of the exterior portion of the body to be operated on. In addition, the retractor disclosed in Scott utilizes elastic members to retract tissue. Because of this, as the tissue is cut at deeper and deeper depths, some slack builds in the elastic tensioning members. To increase the biasing force, the surgeon must manually adjust the tensioning member by repositioning the elastic member the same or a different notch.

There thus is a need for a surgical retractor that is capable of applying a substantially constant biasing force to a portion of tissue without needing to manually readjust the tensioning members. Moreover, the surgical retractor could advantageously be deployed within a body cavity, for example, in laparoscopic applications. For instance, the surgical retractor could enable a single surgeon to perform tissue transection procedures.

SUMMARY OF THE INVENTION

In one embodiment of the invention, a surgical retractor device includes a frame and at least one retracting member configured for being secured to the frame. The retracting member(s) is/are formed as a spring-biased rotatable member having a tension line secured at a proximal end thereto. A tissue securing member is disposed at a distal end of the tension line. The frame may be formed from a flexible material to enable the same to conform to the shape of the tissue to be resected. The flexible frame may also permit the frame to be inserted laparoscopically, for example, via a hand port or the like. The frame may also be collapsible, either by the flexible nature of its construction or through the use of one or more hinges or pivot points. The collapsible frame can then be passed through an access passageway in the patient. For example, the frame may be collapsed and inserted into a body cavity via a hand port or trocar.

The spring-biased rotatable member may be formed as a reel, a flanged spool, or the like that is secured to a torsion spring. In one preferred embodiment of the invention, the at least one retracting member applies a substantially uniform biasing force during retraction of tissue. In this regard, there is no need to reposition the retracting member to adjust the tension on the tissue.

The surgical retractor may have a single retracting member, for example, with one portion of the resected tissue being held manually while a second portion is secured to the retracting member. Alternatively, a plurality of retracting members may be positioned about the frame to apply a biasing force to the resected tissue. Also, the retracting members may be formed such that they can be repositioned as needed.

The surgical retractor may use any number of tissue securing members for affixing the distal end of the tension line to the tissue. For example, the tissue securing members may be formed as a hook, clamp, blade, rake or the like.

In another embodiment of the invention, a surgical retractor system is provided that includes a hand port device that is used to access a passageway within the patient. The system also includes a surgical retractor device that includes a collapsible frame and a plurality of retracting members configured for being secured to the collapsible frame. Each retracting member includes a spring-biased rotatable member and a tension line that is secured at a proximal end to the spring-biased rotatable member. The distal end of the tension line includes a tissue securing member that is used to affix to the resected tissue.

To use the system, a hand port is used to access a passageway that provides access to a body cavity. The surgical retractor device is placed in a collapsed state and inserted into the body cavity via the hand port. The retractor device may collapse based on its inherent flexibility and/or through the use of one or more hinges or pivot points. The surgical retractor device is then positioned over a portion of tissue that is to be resected. The surgical retractor device may need to be expanded during this step. The tissue may include diseased organ tissue such as lung tissue, liver tissue, kidney tissue, and the like. The tissue securing members are then affixed or otherwise secured to the tissue being resected. One or more initial cuts may be needed to form the attachment points needed to secure the tissue securing members.

In one preferred embodiment, each retracting member applies a substantially uniform biasing force during retraction of the tissue. Consequently, as additional tissue is resected, the biasing or traction force remains substantially constant. In this regard, there is no need to reposition the retracting members to apply a larger traction force to compensate for any slack in the system. The spring-biased rotatable member rapidly accommodates any slack that builds in the system as the resection operation proceeds.

In another embodiment of the invention, a method of resecting tissue includes providing an access passageway in a patient. The access passageway may include, for example, a laparoscopic incision made in the skin of the patient. A surgical retractor is then inserted through the access passageway and positioned over a portion of tissue that is to be resected. A hand port may be used to insert the surgical retractor within the body cavity. One or more spring-biased tissue securing members are then secured to the tissue being resected. Each spring-biased tissue securing member applies a substantially uniform biasing force to the resected tissue. After use, the surgical retractor can then be withdrawn from the body cavity via the access passageway.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 8 illustrates the resected line being further exposed as a result of the biasing force from the surgical retractor device.

DETAILED DESCRIPTION OF THE PREFERRED EMBODIMENTS

Figure 1:
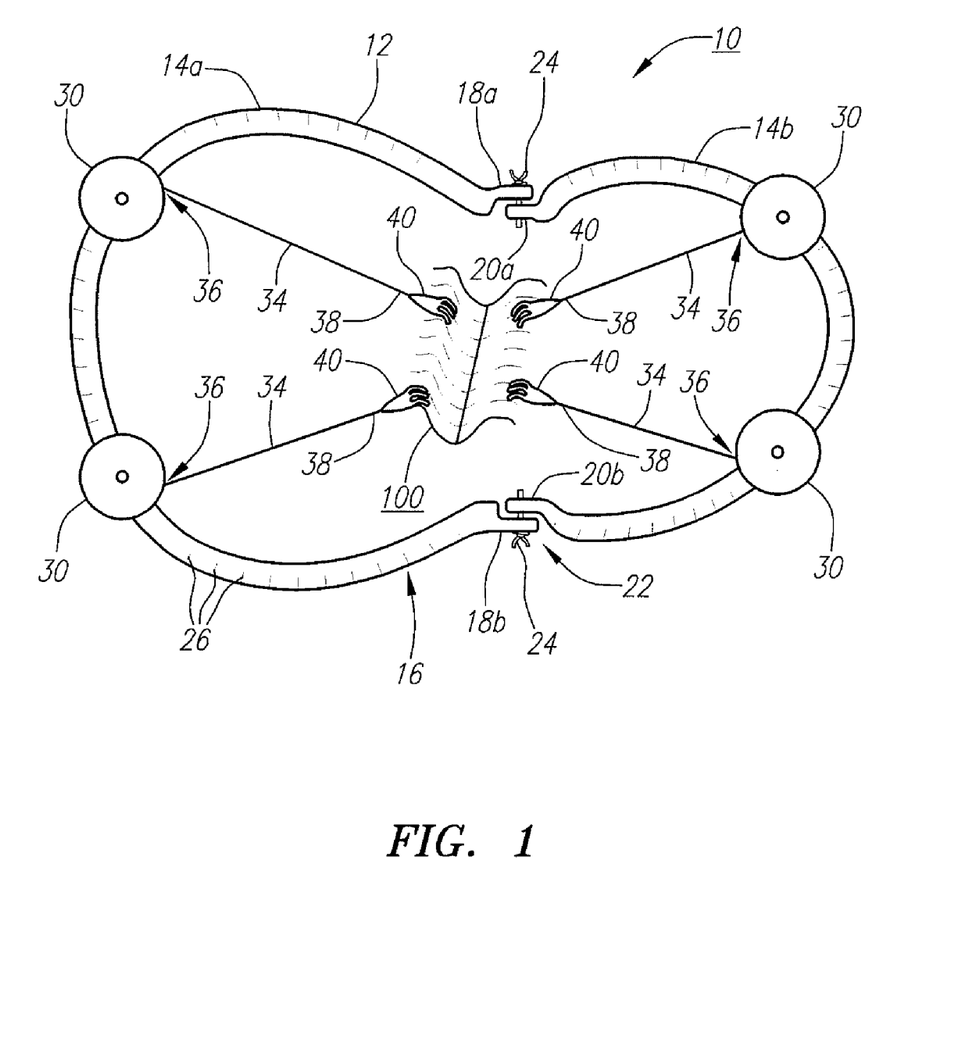
FIG. 1 is a plan view of a surgical retractor device according to one embodiment. A plurality of retractor members are shown retracting a portion of resected tissue.

FIG. 1 illustrates a surgical retractor device 10 according to one embodiment. The surgical retractor device 10 includes a frame 12 which may be formed as a single piece or, alternatively, as shown in FIG. 1, is formed from multiple sub-frames 14a, 14b. The frame 12 defines an outer periphery 16 that generally surrounds a region of tissue 100 that is to be operated on.

The frame 12 in FIG. 1 includes a first sub-frame portion 14a that is generally arcuate or rounded and terminates in ends 18a, 18b. The frame 12 also includes a second sub-frame portion 14b that has a similar shape and terminates in ends 20a, 20b. The second-sub frame portion 14b may be dimensioned such that it can nest within the larger sub-frame portion 14a when in a collapsed configuration (described in more detail below). The first and second sub-frame portions 14a, 14b are connected to one another via a pivot point 22. In one embodiment, bolts 24 or other adjustment members are used to secure the two sub-frame portions 14a, 14b together. The bolts 24 may be threaded through corresponding holes in the ends 18a, 18b, 20a, 20b of the respective first and second sub-frame portions 14a, 14b.

The bolts 24 or other adjustment members may be used to adjust the profile of the overall frame 12. The profile of the frame 12 may be tailored to fit over the region of tissue 100. For example, the sub-frames 14a, 14b may be secured to one another in a generally planar configuration. Alternatively, the sub-frames 14a, 14b may be angled with respect to one another when used, for instance, on a curved region of tissue 100.

In certain embodiments, the frame 12 may be formed from a solid material such as a metal or the like. Alternatively, the frame 12 may be formed from a flexible material such as, for instance, a biocompatible polymer or plastic. A flexible frame 12 may advantageously be used to delivery the surgical retractor device 10 laparoscopically.

While the frame 12 illustrated in FIG. 1 generally has an arcuate-shaped outer periphery 16, it should be understood that various shapes may be used in connection with the surgical retractor device 10. For example, square, circular, rectangular, oblong are but a few shapes that may be used in connection with the frame 12. As stated above, the frame 12 may even be formed as a unitary piece, thereby avoiding the need for sub-frame portions 14a, 14b.

In one embodiment, the frame 12 includes a plurality of notches 26 disposed about the outer periphery 16 of the frame 12. The notches 26 may be used to position one or more retracting members 30 on the frame 12. As an alternative to notches 26, positioning holes or grooves (not shown) may be provided about the outer periphery 16 of the frame to position the retracting members 30.

Figure 4A:
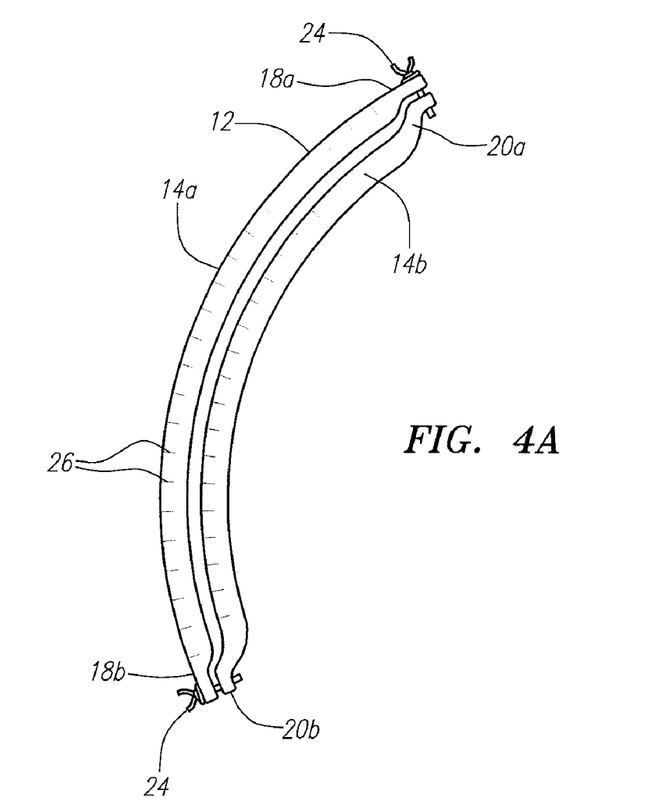
FIG. 4A illustrates a surgical retractor device in a collapsed state according to one embodiment of the invention. The retractor device is shown without the attached retractor member(s).
Figure 4B:
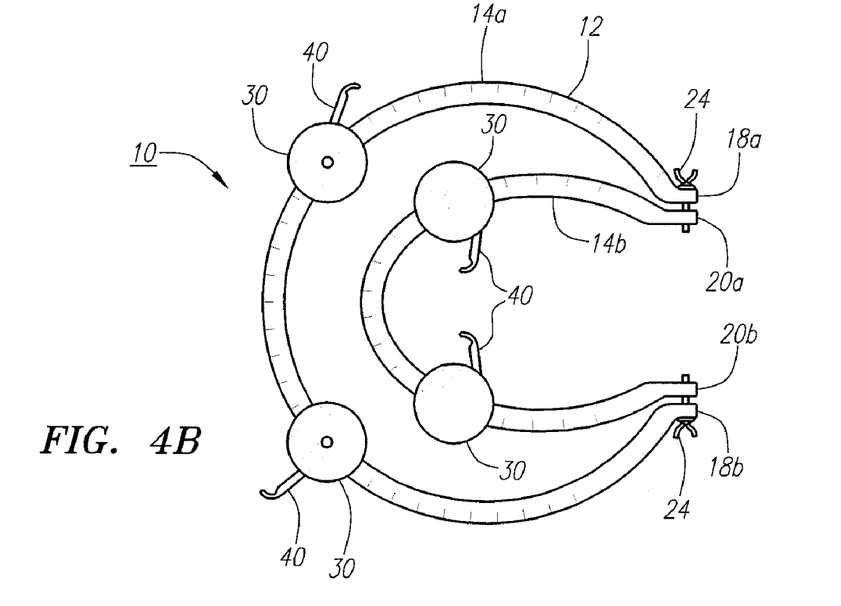
FIG. 4B illustrates a surgical retractor device in a collapsed state according to another embodiment of the invention.

Still referring to FIG. 1, the surgical retractor device 10 includes at least one retracting member 30. FIG. 4B illustrates four retracting members 30 positioned about the frame 12. Each retracting member 30 includes a spring-biased or spring-loaded rotatable member 32. As described in more detail below, the spring-biased rotatable member 32 is rotatably biased in one direction (i.e., clockwise or counter-clockwise directions). A tension line 34 is provided and affixed at or near a proximal end 36 to the spring-biased rotatable member 32. A distal end 38 of the tension line 34 includes a tissue securing member 40. The tissue securing member 40 is used to secure the tension line 34 to the tissue 100 being cut or resected.

Figures 2A, 3:
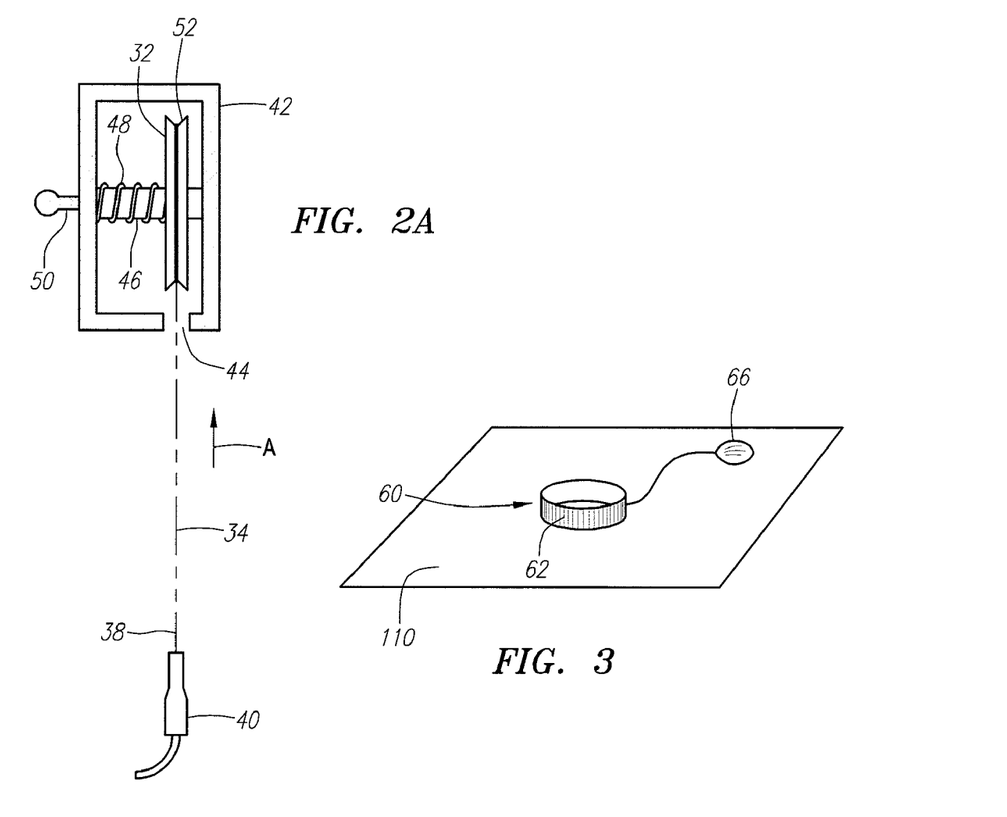
FIG. 2A is a cross-sectional view a retractor member according to one embodiment of the invention.
FIG. 3 illustrates a hand port device being positioned over an access passageway formed in a patient.
Figure 2B:
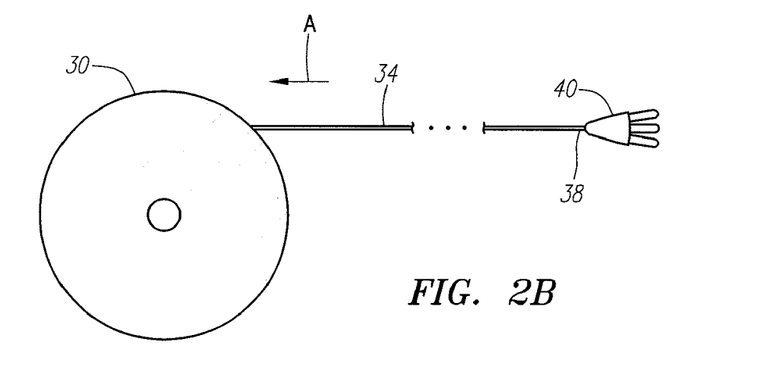
FIG. 2B illustrates a plan view of a retractor member according to one embodiment of the invention.

With reference to FIGS. 1, 2A, and 2B, according to one embodiment, each retracting member 30 is formed within an optional housing 42 having a aperture or hole 44 for passage of the tension line 34. The spring-biased rotatable member 32 is rotatably mounted within the housing 42. For example, the spring-biased rotatable member 32 may be rotatable about an axle 46 or the like. The spring-biased rotatable member 32 may be formed as a reel or the like such as that illustrated in FIG. 2A. In one embodiment, a torsion spring 48 is affixed to the housing 42 and the spring-biased rotatable member 32 to provide the biasing force. In this regard, the spring-biased rotatable member 32 constantly applies tension to the tension line 34 when the tissue securing member 40 is affixed to the tissue 100.

The housing 42 may include a mating member 50 that is used to engage the notches 26 located on the frame 12. The mating member 50 may be formed as a post, knob, or the like that engages with notches 26 in a friction or snap fit. In one preferred embodiment, the mating member 50 is formed such that the retracting member 30 can be repositioned about periphery of frame 12. For example, if the physician wants a different angle of retraction with respect to the tissue 100, the physician can reposition the retracting member(s) 30 to the appropriate position(s).

The spring-biased rotatable member 32 may be flanged or have a central groove 52 on which the tension line 34 is positioned. In its fully retracted position, the tension line 34 is rolled around an exterior surface of the spring-biased rotatable member 32. The tension line 34 is then unrolled as the tissue securing member 40 is pulled away from housing 42.

As seen in FIGS. 2A and 2B, the natural biasing force of the retracting member 30 tends to pull the tissue securing member 40 (and secured tension line 34) into the housing 42 in the direction of arrows A. Retraction of the tissue securing member 40 is accomplished by rotation of the spring-biased rotatable member 32 in either the clockwise or counter-clockwise direction. In one preferred embodiment, the retracting member 30 applies a substantially uniform biasing force during retraction of the tissue 100.

The tissue securing member 40 located at the distal end 38 of the tension line 34 may be formed has a hook, clamp, blade, rake (shown in FIGS. 1, 2A, 2B), or the like. During the surgical procedure, the tissue securing member 40 is secured or otherwise affixed to the tissue 100. The tissue securing members 40 may be formed such that they can be repositioned as needed by the surgeon.

With reference to FIGS. 3 through 8 a description of the use of the surgical retractor device 10 according to one embodiment will now be given. In this embodiment, the surgical retractor device 10 is delivered laparoscopically. FIG. 3 illustrates a portion of exposed skin 110 of a patient. For example, the exposed skin 110 may be located in the torso region of the patient. A hand port device 60 is positioned over or around an access passageway such as an incision made in the skin 110 of the patient. The hand port device 60 allows the surgeon to position his or her hand within the body cavity of the patient during the surgical procedure. The hand port device 60 is generally formed as a ring 62 and may include an inflatable portion 64 (best seen in FIGS. 5 and 6) that seals the internal body cavity from the external environment. The inflatable portion 64 is inflated with using a coupled pump 66.

In laparoscopic procedures, air or other insufflation gas is introduced into the body cavity to provide a working space. If an access port is provided in the body cavity for passage of a hand, for example, there needs to be a way to substantially seal the body cavity to prevent the air from leaking to the external environment. The inflatable hand port device 60 is one way to provide such a seal. Other hand ports 60 operate by using a dedicated valve member or even a gel to seal the opening. These other types of hand ports 60 may also be used in connection with the surgical retractor device 10 described herein.

In this embodiment, the surgical retractor device 10 is inserted laparoscopically within the patient. In order to fit the surgical retractor device 10 within the access passageway inside the hand port, the surgical retractor device 10 is transformed or adjusted into a collapsed state. FIGS. 4A and 4B illustrate two embodiments of a surgical retractor device 10 in the collapsed state. In FIG. 4A, the frame 12 is formed from a flexible material. In this regard, the arcuate or rounded nature of the frame (as is shown, for example, in FIG. 1) is adjusted to a straight or slightly bent configuration. This reduces the overall size of the surgical retractor device 10 to permit the same to be inserted into the body cavity of the patient via the hand port 60.

As seen in FIG. 4A, the retracting members 30 are shown removed from the frame 12. For example, the frame 12 may be inserted into the body cavity of the patient first. The one or more retracting members 30 may then be passed individually through the hand port 60 and secured to the frame 12 via the mating members 50. Alternatively, the retracting members 30 may be pre-positioned on the frame 12.

FIG. 4B illustrates another embodiment of a surgical retractor device 10 in a collapsed state. In FIG. 4B, the retracting members 30 are shown attached to the frame 12. The tension line 34 is withdrawn inside the retracting members 30, leaving the tissue securing members 40 positioned just outside the housing 42. The surgical retractor device 10 can then be inserted into the body cavity via the hand port 60. For example, the surgical retractor device 10 may be feed into the body cavity by first inserting one of the ends 18a, 18b, 20a, 20b of the respective first and second sub-frame portions 14a, 14b.

In order to transform the retractor device 10 into the collapsed state, one or both of the bolts 24 coupling the sub-frames 14a, 14b may be loosened or removed entirely to adjust the frame 12 into the collapsed or folded configuration. In the case of a unitary or single-piece frame 12, the frame 12 may be formed of a flexible material to enable the device 10 to be inserted laparoscopically within the patient. For example, the frame 12 may be folded onto itself. Alternatively, the frame 12 may have one or more pivot points that enables the frame 12 to collapse into a smaller size suitable for laparoscopic insertion.

Figure 5:
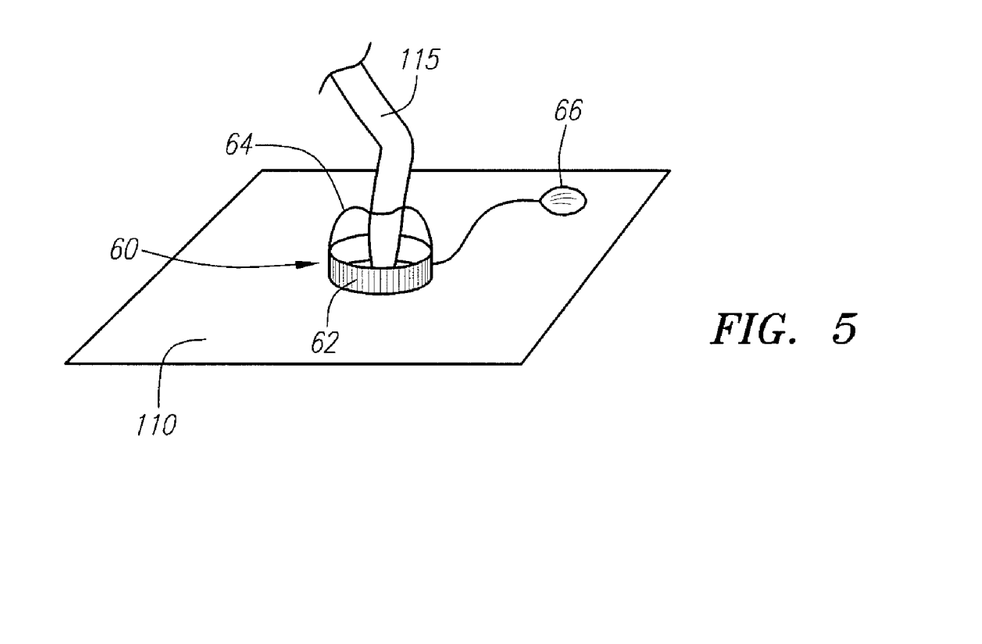
FIG. 5 illustrates a physician's hand accessing the patient's body cavity via a hand port device.

FIG. 5 illustrates a surgeon's hand 115 being inserted into the patient's body cavity via the hand port device 60. The surgeon manually inserts the surgical retractor device 10 into the body via an access passageway such as an incision in the patient's skin 110. The retractor device 10 is inserted in the collapsed configuration as described previously. The pump 66 on the hand port device 60 is used to expand the inflatable portion 64 to substantially seal the body cavity from the external environment. The hand port device 60 permits the surgeon to gain tactile sensitivity during the surgical procedure. In this regard, the hand port device 60 combines the laparoscopic benefits with the advantages of a conventional "open" approach. Typically, the surgeon will insert his or her non-dominant hand 115 into the abdominal cavity via the hand port device 60.

Figure 6:
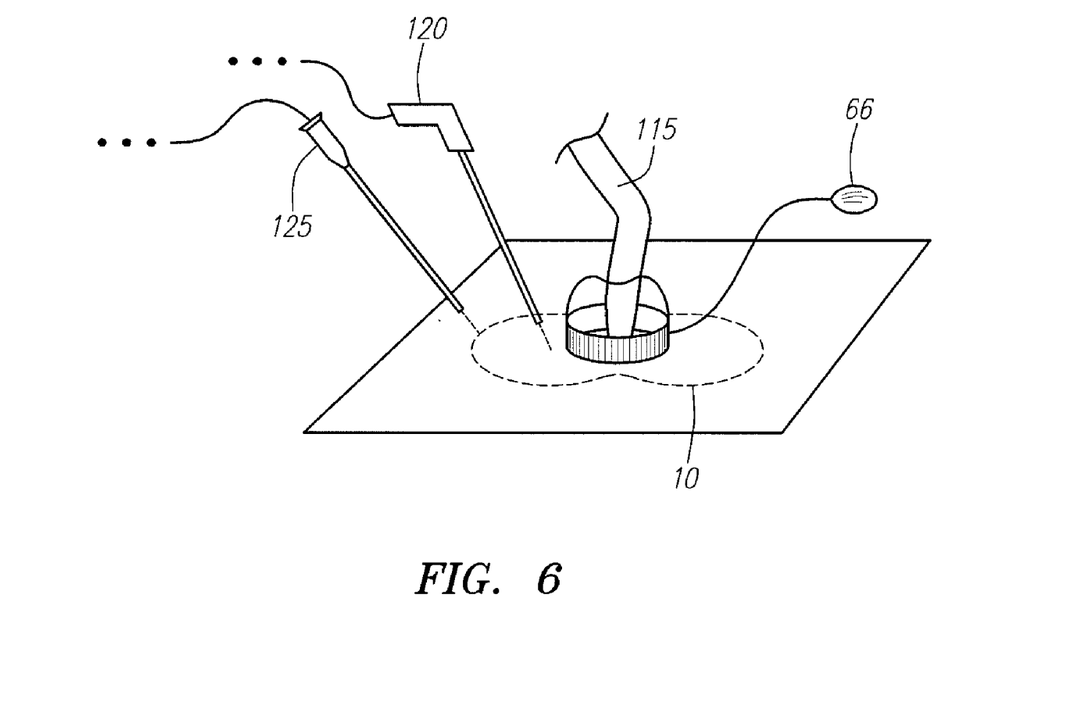
FIG. 6 illustrates a surgical retractor device being positioned laparoscopically within a patient's body cavity. Additional surgical tools are shown accessing the patient's body cavity.

FIG. 6 illustrates the surgical retractor device 10 (shown in phantom by dashed lines) placed within the body cavity of the patient. The retractor device 10 is shown in its expanded state. In one embodiment, the retractor device 10 is expanded manually within the body cavity of the patient. For example, the operating surgeon may use his or her hand to adjust the frame 12 into the open or expanded state. This may involve rotating the frame 12 about one or more pivot points or hinges. Likewise, the operating surgeon may need to adjust or manipulate one or more bolts 24 on the frame 12 to expand the frame 12 to its desired shape.

Alternatively, the frame 12 may open automatically upon placement inside the patient's body cavity. For example, if the frame 12 is made of a flexible material, the retractor device 10 may automatically open from a collapsed or folded configuration into an expanded configuration such as that shown in FIG. 6. After opening of the frame 12, the surgeon may need to adjust or fine tune the placement of the surgical retractor device 10 within the body cavity. The frame 12 may be positioned or float above the tissue region of interest. In this manner, the frame 12 is not adhered to the tissue. Alternatively, the frame 12 may be temporarily secured to the tissue using an adhesive or sutures.

FIG. 6 also illustrates additional surgical tools 120, 125 that are inserted into the body cavity of the patient. For example, a cutting or resection device 120 may be inserted laparoscopically into a small incision made in the exposed skin 110 of the patient. The cutting or resection device 120 may use a mechanical cutting member such as a blade or the like. Alternatively, for example, the cutting or resection device 120 may be a radiofrequency (RF) based electrosurgical device that uses RF energy to cut or resect tissue. It should be understood that the invention is not limited by the type of cutting device 120 used. The surgical resection device 10 may be used in connection with any means of cutting tissue known to those skilled in the art.

Additional surgical tools 125 may also be inserted into the body cavity through a laparoscopic incision in the exposed tissue 100 of the patient. For example, tool 125 may include a suction device that is coupled to a source of vacuum that can remove blood and other material from the surgical site. Alternatively, the tool 125 may include an imaging device to permit the surgeon to visualize the operation on an external monitor or the like (not shown).

During the surgical procedure, a single surgeon is able to manipulate the cutting device 120 to perform the cutting or resection operation. For instance, one hand of the physician may be placed inside the patient's body cavity to provide tactile feedback. The surgeon's remaining hand may be used to manipulate the cutting device 120 and or surgical tool(s) 125.

Figure 7:
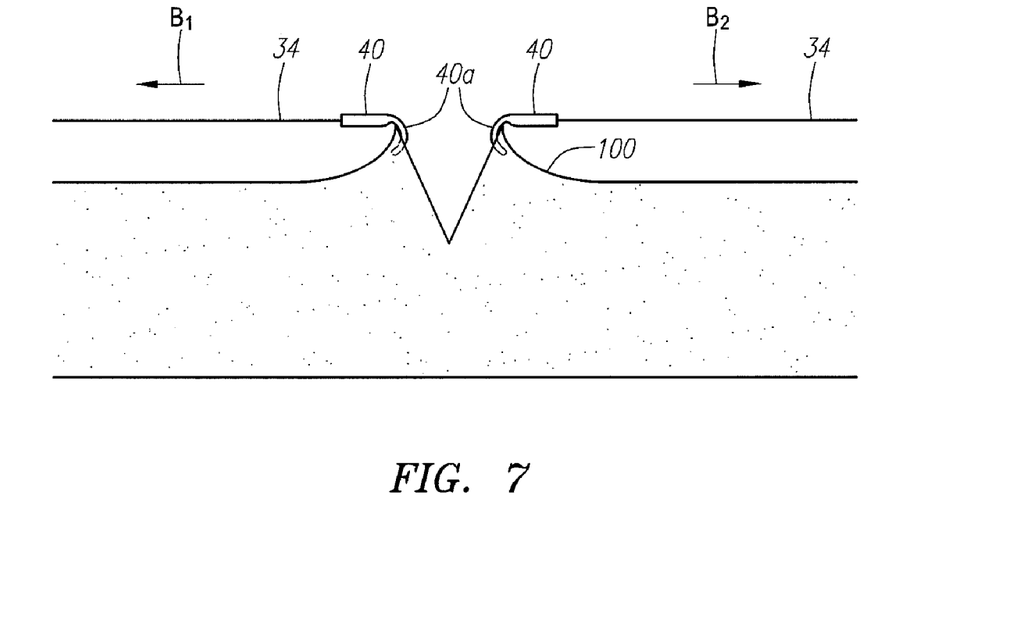
FIG. 7 is a cross-sectional view of tissue being resected using the surgical retractor device. Spring-biased tension lines are shown pulling apart the resected tissue in generally opposite directions.
Figure 8:
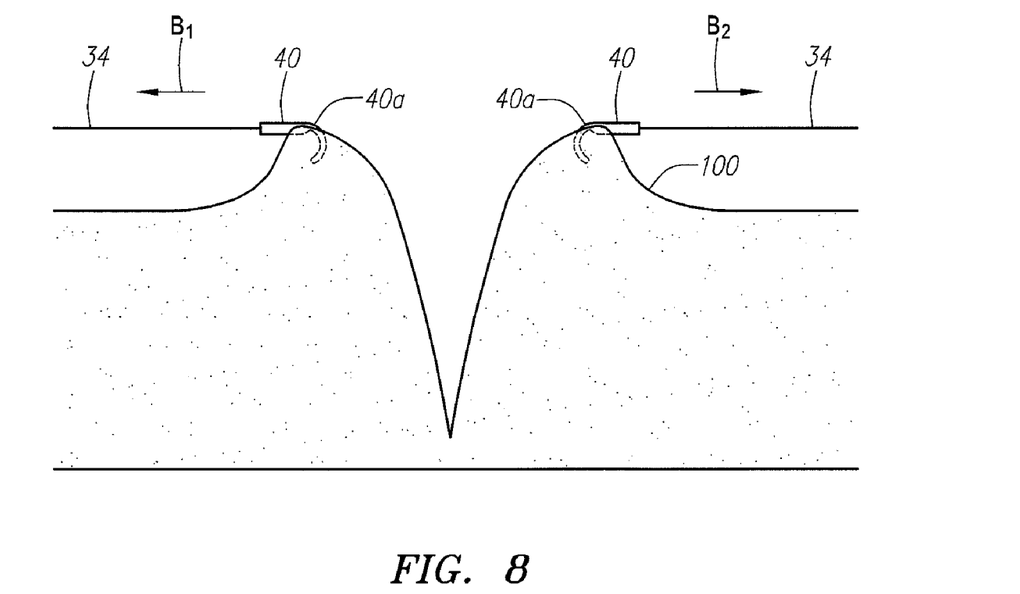
FIG. 8 is a cross-sectional view of the tissue shown in FIG. 7 after additional cutting or resection has been performed.

As best seen in FIGS. 7 and 8, the surgical retractor device 10 applies a biasing force to the resected tissue 100. In FIG. 7, two tissue securing members 40 are shown being secured to portions of the resected tissue 100. The tissue securing members 40 are positioned on or near the site of cutting or resection. The tissue securing members 40 are shown with hooks 40a that penetrate within the resected tissue 100. The tension lines 34 apply a biasing force to the resected tissue 100 in the direction of arrows $B_1$ and $B_2$.

FIG. 8 illustrates the same tissue 100 after the resection or cutting line has grown deeper within the tissue 100. As seen in FIG. 8, the resected or cut tissue 100 is pulled further apart by the biasing force of the securing members 40. In this regard, the resection device 10 exposes the growing resection line to assist the surgeon during the procedure.

After the operation is complete, the resection device 10 is removed from the body cavity via the hand port device 60. The frame 12 of the resection device 10 may need to be collapsed prior to removal. In this case, the surgeon may fold, bend, or twist the frame 12 into a smaller, collapsed state. In certain embodiments, this may require the surgeon to adjust or remove one or more bolts 24 positioned on the frame 12. Once the frame 12 is in the collapsed configuration, the resection device 10 can be easily removed from the body cavity via the hand port device 60.

As an alternative to delivery via a hand port device 60, the resection device 10 may be delivered via a trocar (not shown). In this embodiment, the frame 12 of the resection device 10 should be made of a flexible material to permit the same to fit within the relatively narrow lumen of the trocar.

The surgical retractor device 10 may be used to cut or resect any number of tissue and/or organ types. For example, the surgical retractor device 10 may be used on liver, kidney, lung, vaginal, urological, colorectal tissues. It should also be understood that the surgical retractor device 10 may be used in non-laparoscopic surgical procedures (e.g., intraoperative procedures). For example, the surgical retractor device 10 may be used on an external surface of the patient.

One important benefit of the surgical retractor device 10 is that surgeries that once required multiple surgeons may now be performed by a single surgeon. For example, the current two-surgeon technique for liver transection described in Aloia et al., may be performed by a single surgeon. There is no need for a second person to assist in providing traction to the resected tissue.

While embodiments of the present invention have been shown and described, various modifications may be made without departing from the scope of the present invention. The invention, therefore, should not be limited, except to the following claims, and their equivalents.

What is claimed is:

1. A surgical retractor device comprising:
    a frame comprising a plurality of notches disposed about a periphery of the frame;
    at least one retracting member configured for being secured to the frame, the at least one retracting member comprising:
        a housing containing a post at one end thereof, the post configured to engage with one of the plurality of notches disposed about the periphery of the frame;
        a spring-biased rotatable member rotationally mounted on an axle within the housing, the spring-biased rotatable member being operatively coupled to a torsion spring affixed at one end to the housing;
        a tension line secured at a proximal end to the spring-biased rotatable member; and
        a tissue securing member disposed at a distal end of the tension line,
        wherein the spring-biased rotatable member is biased to null the tension line and the tissue securing member into the housing.

2. The surgical retractor device of claim 1, wherein the frame is flexible.

3. The surgical retractor device of claim 1, wherein the frame is collapsible.

4. The surgical retractor device of claim 1, wherein the surgical retractor is configured for passage through a hand port.

5. The surgical retractor device of claim 1, wherein the torsion spring is mounted on the axle.

6. The surgical retractor device of claim 1, wherein the at least one retracting member comprises a plurality of retracting members.

7. The surgical retractor device of claim 6, wherein each of the plurality of retracting members applies a substantially uniform biasing force during retraction of tissue without the need for subsequent adjustment.

8. The surgical retractor device of claim 1, wherein the at least one retracting member applies a substantially uniform biasing force during retraction of tissue without the need for subsequent adjustment.

9. The surgical retractor device of claim 1, wherein the post is configured to be removed from one of the plurality of notches and engagable with another of the plurality of notches.

10. The surgical retractor device of claim 1, wherein the frame includes a plurality of sub-frames and one or more hinges coupling the plurality of sub-frames.

11. A surgical retractor system comprising:
 a hand port device;
 a surgical retractor device comprising:
  a collapsible frame comprising a plurality of notches disposed about a periphery of the frame;
  a plurality of retracting members configured for being secured to individual notches of the collapsible frame, each of the plurality of retracting members comprising a housing containing a post at one end thereof configured to engage with one of the plurality of notches disposed about the periphery of the frame, each housing containing therein an axle holding a reel, the reel being operatively coupled to a torsion spring affixed at one end to the housing, a tension line secured at a proximal end to the reel, and a tissue securing member disposed at a distal end of the tension line,
 wherein the reel is biased to null the tension line and the tissue securing member into the housing.

12. The surgical retractor system of claim 11, wherein the torsion spring is mounted on the axle.

13. The surgical retractor system of claim 12, wherein the plurality of retracting members are configured to be removed from one of the plurality of notches and engagable with another of the plurality of notches.

14. The surgical retractor system of claim 11, wherein each of the plurality of retracting members applies a substantially uniform biasing force during retraction of tissue without the need for subsequent adjustment.

\* \* \* \* \*

UNITED STATES PATENT AND TRADEMARK OFFICE
CERTIFICATE OF CORRECTION

PATENT NO. : 7,691,058 B2
APPLICATION NO. : 11/424483
DATED : April 6, 2010
INVENTOR(S) : Robert F. Rioux et al.

Page 1 of 1

It is certified that error appears in the above-identified patent and that said Letters Patent is hereby corrected as shown below:

Claim 1, col. 8, line 57, "null" should read -- pull --.

Claim 11, col. 10, line 11, "null" should read -- pull --.

Signed and Sealed this

Twenty-fourth Day of August, 2010

David J. Kappos
*Director of the United States Patent and Trademark Office*